(12) United States Patent
Wang et al.

(10) Patent No.: US 9,834,732 B2
(45) Date of Patent: Dec. 5, 2017

(54) DEVELOPMENT AND IMPLEMENTATION OF ANALYZER BASED CONTROL SYSTEM AND ALGORITHM

(71) Applicant: Nalco Company, Naperville, IL (US)

(72) Inventors: Jin Wang, Houston, TX (US); Nigel P. Hilton, Houston, TX (US); Glenn L. Scattergood, Shanghai (CN); Sam Ferguson, Sugar Land, TX (US)

(73) Assignee: Nalco Company LLC, Naperville, IL (US)

( * ) Notice: Subject to any disclaimer, the term of this patent is extended or adjusted under 35 U.S.C. 154(b) by 0 days.

(21) Appl. No.: 15/284,770

(22) Filed: Oct. 4, 2016

(65) Prior Publication Data

US 2017/0051215 A1    Feb. 23, 2017

Related U.S. Application Data

(63) Continuation of application No. 13/557,761, filed on Jul. 25, 2012, now Pat. No. 9,458,388.

(51) Int. Cl.

| | |
|---|---|
| *C10G 7/10* | (2006.01) |
| *C10G 75/02* | (2006.01) |
| *G05B 23/02* | (2006.01) |
| *G01N 17/02* | (2006.01) |

(52) U.S. Cl.
CPC ......... *C10G 75/02* (2013.01); *G05B 23/0221* (2013.01); *G01N 17/02* (2013.01)

(58) Field of Classification Search
CPC ....................................................... C10G 7/10
See application file for complete search history.

(56) References Cited

U.S. PATENT DOCUMENTS

| | | | |
|---|---|---|---|
| 3,740,722 A | 6/1973 | Greenberg et al. | |
| 3,779,905 A | 12/1973 | Stedman | |
| 3,819,328 A | 6/1974 | Go | |
| 4,238,349 A | 12/1980 | Larsen et al. | |
| 4,317,182 A | 2/1982 | Takase et al. | |
| 4,335,072 A | 6/1982 | Barnett et al. | |
| 4,425,267 A | 1/1984 | Skripchik et al. | |
| 5,066,199 A | 11/1991 | Reese et al. | |
| 5,094,958 A * | 3/1992 | Klainer ................ | G01N 21/648 250/227.23 |
| 5,195,879 A | 3/1993 | Reese et al. | |
| 5,256,276 A | 10/1993 | Weaver | |
| 5,302,253 A | 4/1994 | Lessard et al. | |
| 5,324,665 A | 6/1994 | Lessard et al. | |
| 5,326,482 A | 7/1994 | Lessard et al. | |
| 5,425,267 A | 6/1995 | Herrmann et al. | |
| 5,503,006 A | 4/1996 | Babaian-Kibala et al. | |
| 5,965,785 A * | 10/1999 | Braden ................... | C10G 7/10 208/184 |
| 7,744,276 B2 | 6/2010 | Webb | |
| 8,712,335 B2 | 4/2014 | Mathur et al. | |
| 2007/0025412 A1 | 2/2007 | Webb | |
| 2007/0077176 A1 | 4/2007 | Lambert et al. | |
| 2007/0152813 A1 | 7/2007 | Mathur et al. | |
| 2009/0149981 A1 | 6/2009 | Evans et al. | |
| 2010/0108566 A1* | 5/2010 | Scattergood ............. | C10G 7/10 208/47 |
| 2011/0282614 A1 | 11/2011 | Kiyono | |
| 2012/0053861 A1* | 3/2012 | Kremer ................... | C10G 75/02 702/50 |
| 2012/0092646 A1 | 4/2012 | Stolberg-Rohr et al. | |
| 2014/0053837 A1 | 2/2014 | Klein | |

FOREIGN PATENT DOCUMENTS

| | | |
|---|---|---|
| CN | 101273313 A | 9/2008 |
| EP | 1298185 A1 | 4/2003 |
| GB | 1198734 A | 7/1970 |
| JP | 55-116101 A | 9/1980 |
| JP | 2008-262482 A | 10/2008 |
| JP | 2009-282750 A | 12/2009 |
| JP | 2010-210588 A | 9/2010 |
| JP | 2010-215882 A | 9/2010 |
| JP | 2011-122823 A | 6/2011 |
| JP | 2012-507612 A | 3/2012 |
| WO | WO 03/006581 A2 | 1/2003 |
| WO | WO 2004/044266 A1 | 5/2004 |
| WO | WO 2007/037988 A1 | 4/2007 |
| WO | WO 2008/005058 A1 | 1/2008 |
| WO | WO 2010/062728 A1 | 6/2010 |

OTHER PUBLICATIONS

Conant, "Wireless Sensor Networks: Driving the New Industrial Revolution," Industrial Embedded Systems, Apr. 2006, 4 pp.
European Patent Office, Extended European Search Report in European Patent Application No. 13823686.4, May 30, 2016, 8 pp.
Korean Patent Office, International Search Report in International Patent Application No. PCT/US2013/051932, Nov. 6, 2013, 3 pp.
Korean Patent Office, Written Opinion in International Patent Application No. PCT/US2013/051932, Nov. 6, 2013, 4 pp.
Little et al., "How to Control . . . Crude Unit Overhead Corrosion," *Hydrocarbon Processing*, 56(5), 1977, pp. 205-207.
Szyprowski et al., "Anticorrosion Technology Demonstrated at Polish Refinery," *Oil and Gas Journal*, 85(18), 1987, pp. 33-37.
Zimmerschied et al., "Nonlinear time constant estimation and dynamic compensation of temperature sensors," *Control Engineering Practice*, 18(3), Mar. 2010, pp. 300-310.
European Patent Office, Extended European Search Report in European Patent Application No. 13823686.4, dated May 30, 2016, 8 pp.

\* cited by examiner

*Primary Examiner* — Randy Boyer
(74) *Attorney, Agent, or Firm* — Leydig, Voit & Mayer, Ltd.

(57) ABSTRACT

A method of correcting measurements of a chemical sensor used in an industrial facility. The method involves correcting for errors known to occur in the steady state and the dynamic state for specifically recognized situations. This method allows for correcting errors that occur due to deadtime, false zero measurements, and non-linear disturbances. The method combines automated measurement techniques and human know how to progressively learn and refine the accuracy of the corrections.

12 Claims, 6 Drawing Sheets

Process Performance Evaluation

Critical Variable Performance Index (CVPI)

| Processes | Date Time | Critical Variable | Tag name | Expectation | cp | cpk Index | Performance Improved | Comment |
|---|---|---|---|---|---|---|---|---|
| PRSI | Sept 2013 | pH | | [6.0 7.0] | | | Good | Except events |
| | | Cl | | [0 30] | | | Good | Except events |
| | | Fe | | [0 1] | | | Good | Except events |
| | | Corrosion Rate | CE1C IN | <5mpy | | | Good | reliable |
| | | Corrosion Rate | CE1C OUT | <5mpy | | | Good | too noisy |
| | | Corrosion Rate | CE1A IN | <5mpy | | | Good | exclude outliers |
| | | Corrosion Rate | CE1A OUT | <5mpy | | | Good | too noisy |
| | | Neutralizer% | | <50%(Man) | | | -32.87 | Compared to Manual |
| | | Filmer% | | <65%(Man) | | | -42.63 | Compared to Manual |
| | | Caustic% | | <45%(Man) | | | -39.34 | Compared to Manual |
| | | Analyzer Service | | | | | | |
| | | Alarm | | <1 week | | | Good | |
| | | Auto on stream time | | >99% | | | Good | |

FIGURE 6

DEVELOPMENT AND IMPLEMENTATION OF ANALYZER BASED CONTROL SYSTEM AND ALGORITHM

CROSS-REFERENCE TO RELATED APPLICATIONS

This application is a continuation of U.S. patent application Ser. No. 13/557,761, filed Jul. 25, 2012, issued on Oct. 4, 2016, as U.S. Pat. No. 9,458,388, which itself is related to U.S. patent application Ser. No. 12/263,904, filed Nov. 3, 2008, the disclosures of which are incorporated by reference herein in their entirety for all purposes.

STATEMENT REGARDING FEDERALLY SPONSORED RESEARCH OR DEVELOPMENT

Not Applicable.

BACKGROUND OF THE INVENTION

This invention relates generally to an analyzer based control system and algorithm for the use in a chemical process system. As described for example in U.S. Pat. Nos. 5,503,006, 5,425,267, 5,965,785, 5,326,482, 4,335,072, U.S. Published Patent Applications 2010/0108566 and 2012/0053861 A1, UK Patent 1,198,734, and International Patent Applications 2008/005058, 2004/044266, and 03/006581, chemical and industrial facilities utilize a variety of complex equipment, which are often subject to harsh chemical and physical conditions. As such, a number of technologies have been developed to monitor the condition, efficiency, and expected lifespan of the equipment. Such technologies include historian systems, which collect and archive data from various sources within the chemical plant. U.S. patent application Ser. No. 12/899,250 describes a number of methods of utilizing historian and other data.

Monitoring equipment typically involves a system in which a variety of process variables are measured and recorded. One such system is described in U.S. Published Patent Application 2009/0149981 A1. Such systems however often produce massive amounts of data of which only a small portion of which is usefully tracked to detect abnormal conditions and the information gleaned from those systems is of limited practical use.

In the context of corrosion prevention, three of the most useful data sets for a monitor to measure are pH, metal (especially iron) ion concentrations, and chloride ion concentrations. Ideally the monitored data is as close to real time as possible so remediation techniques for the causes of extreme concentrations can be applied before the causes effect corrosion or otherwise damage the facility. Unfortunately current monitoring technologies provide a large volume of false data so real time monitoring is usually difficult if not impossible. Moreover the false data can lead to the wasting of expensive remedial chemistries when their addition was not needed. As a result a truly automated remedial chemical feed system is not feasible and a human operator is typically required to prevent the addition of remediating chemicals in the face of a "false alarm" thereby increasing operation costs.

Thus there is a clear need for and utility in an improved method of monitoring the conditions within a chemical plant. The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

BRIEF SUMMARY OF THE INVENTION

At least one embodiment of the invention is directed towards a method of correcting an error in the measurement of a process variable taken by a sensor in a chemical process system. The system is characterized by properties which cause at least some of the measurements to be erroneous. The method comprises the steps of: 1) identifying the component of the error caused by dynamic state factors, this component of the error being determined by at least once obtaining a senor measurement in the system and noting how that measurement deviates from an objectively correct measurement of the process variable by varying amounts relative to time, 2) identifying the steady state factor component of the error, this component of the error being determined by at least once obtaining a senor measurements and noting that the measurement deviates from the objectively correct measurement of the process variable by a fixed amount relative to time, 3) identifying the component of the error caused by additional factors, and 4) altering the measurement to remove the errors caused by steady state factors, dynamic state factors, and unknown factors.

The sensor may be in informational communication with an analyzer and the analyzer may be in informational communication with a controller. The sensor may be constructed and arranged to obtain a raw measurement of the process variable. The analyzer may correct the error in the sensor's measurement. The controller may take the corrected measurement. If the corrected measurement is outside of a pre-determined range of acceptable values, it may enact a remedial measure to change the measured value to a value within the acceptable range. The remedial measure may be enacted before the steady state value of the measurement is detected by the sensor.

The process variable may be a measurement of one item selected from the list consisting of: oxidation-reduction potential, pH, levels of certain chemicals or ions (e.g., determined empirically, automatically, fluorescently, electrochemically, colorimetrically, measured directly, calculated), temperature, pressure, process stream flow rate, dissolved solids and suspended solids.

There may be at least three sensors and each of the three sensors may pass on a raw measurement to the analyzer. The analyzer may use the average of those raw measurements as the input in its calculations if at least one of the raw measurements fits within a pre-determined setpoint expected for the specific conditions under which measurement was taken, the analyzer a historically expected value as the input in its calculations if none of the raw measurements fit within a pre-determined setpoint expected for the specific conditions under which measurement was taken, The process variable may be iron concentration. The method may further comprise the steps of: disregarding all sensor readings that indicate zero iron concentration, and adjusting the measured iron concentrations using regression analysis over a 1 week time period. The remedial measure may involve adding a chemical whose effect is non-linear in nature. The analyzer may correct for the non-linear effects of the remedial chemical in its corrections. The remedial measure may involve adding a chemical subject to the constraints of deadtime and the analyzer corrects for those effects in its measurements. The process system may be one item selected from the list consisting of: a chemical plant, a refinery, an oil refinery, a food processing facility, a manufacturing plant, a chemical plant, a distillation column, a water filtration plant, a factory, a waste processing facility, a water treatment facility, and any combination thereof.

BRIEF DESCRIPTION OF THE DRAWINGS

A detailed description of the invention is hereafter described with specific reference being made to the drawings in which.

DETAILED DESCRIPTION OF THE INVENTION

The following definitions are provided to determine how terms used in this application, and in particular how the claims, are to be construed. The organization of the definitions is for convenience only and is not intended to limit any of the definitions to any particular category.

"Chemical process system" means one or more processes for converting raw materials into products which includes but is not limited to industrial processes which utilize one or more of the following pieces of equipment: chemical plant, refinery, furnace, cracker, overhead column, stripper, filter, distiller, boiler, reaction vessel, and heat exchanger, and the like.

"Dynamic State" means a condition of a measured process variable in which the observed measurement changes over at least a portion of a discrete period of time during which the condition is measured while in fact the actual magnitude of the process variable is not changing.

"Steady state" means a condition of a measured process variable in which the observed measurement remains unchanging over a discrete period of time during which the condition is measured while in fact the actual magnitude of the process variable is not changing.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology*, 5th Edition, (2005), (Published by Wiley, John & Sons, Inc.) this definition shall control how the term is to be defined in the claims.

Automation technology plays a significant role in improving and maintaining efficient process operation. It influences the strategic and operational goals of enterprises, their economic results, the development and quality of products, continuity of production, and competitiveness in the marketplace. These strategies should include (1) Improvements of unit operation and (2) Optimizing proper selected chemicals. The key to controlling the corrosion rate is to analyze the corrosion performance and drive the decisive knowledge based on operating data and analyzer measurements. Crude Unit Automation (CUA) system is designed to monitor and analyze the system corrosion and feedback control the chemicals using automation technologies. The implementation of these strategies resulted in lower corrosion risk and continued improvement of the run length of the overhead heat exchangers.

In at least one embodiment of the invention, the control system in use in the process system comprises two elements: (1) at least one sensor and (2) at least one analyzer. In at least one embodiment of the invention, the control system comprises three elements: (1) at least one sensor, (2) at least one analyzer, and (3) at least one controller. The sensor(s) is constructed and arranged to measure at least one process variable within at least one portion of the system.

The analyzer receives the measurement taken by the sensor and converts it into information which can be output. The controller receives the output and can cause some operation to occur in response to the output.

In at least one embodiment the response includes adding a chemical. Added chemicals may include neutralizer, filmer, caustic, and inhibitors and so on and are used to control corrosion process variables. The analyzer provides on-line measurements of process variables (especially pH, [Cl] and [Fe]). The analyzer provides output which is used to monitor, analyze and manage the whole system.

In at least one embodiment some or all of the information is displayed on a dashboard. The dashboard can also display how the system manages historian database data, reports, alarms, and make readily available the user's selected strategy for real time control and optimization of the crude unit system.

In at least one embodiment the system is a closed loop which utilizes preliminary analysis of historian and archived data, updates from the analyzer and other diagnostics (such as personal observations and discussions with operating staff) to then generate responses and further analysis of the crude unit's operations.

In at least one embodiment the use of inhibitors is to prevent or to reduce general corrosion, and it plays an important role in the control of corrosion for those areas in which general corrosion is the problem. The objective of the control system is how to prevent/reduce corrosion in crude unit overhead by controlling the inhibitors. As one of the main components of a crude unit process, corrosion control plays a vital role in maintaining system integrity. This invention provides a way to optimize the corrosion control component of the crude unit through optimizing one or more system parameters in a process stream of the crude unit. This optimization includes measuring properties associated with those parameters in the process stream.

In at least one embodiment the analyzer is designed to reduce corrosion of refinery processing equipment and subsequent fouling due to deposition of corrosion byproducts. A typical corrosion control program includes components such as a neutralizing amine, a filming inhibitor, a caustic solution, etc. Such corrosion control chemicals are traditionally injected into the system based upon measurements derived from grab samples and analyzed in the lab or some flow indication on the unit. This invention provides an automated method of adjusting chemical injection into the system.

In at least one embodiment, the method of the invention includes a controller operable to receive and process information and provide instructions to various components (e.g., chemical injection pumps). The term "controller" refers to a manual operator or an electronic device having components such as a processor, memory device, digital storage medium, cathode ray tube, liquid crystal display, plasma display, touch screen, or other monitor, and/or other components. The controller is preferably operable for integration with one or more application-specific integrated circuits, programs, computer-executable instructions or algorithms, one or more hard-wired devices, wireless devices, and/or one or more mechanical devices. Moreover, the controller is operable to integrate the feedback, feed-forward, or predictive loop(s) of the invention. Some or all of the controller system functions may be at a central location, such as a network server, for communication over a local area network, wide area network, wireless network, interne connection, microwave link, infrared link, and the like. In addition, other components such as a signal conditioner or system monitor may be included to facilitate signal transmission and signal-processing algorithms.

The controller may include hierarchy logic to prioritize any measured or predicted properties associated with system parameters. For example, the controller may be programmed to prioritize system pH over chloride ion concentration or vice versa. It should be appreciated that the object of such hierarchy logic is to allow improved control over the system parameters and to avoid circular control loops.

In at least one embodiment, the method includes an automated controller. In another embodiment, the controller is manual or semi-manual. For example, where the crude refining process includes one or more datasets received from a various sensors in the system, the controller may either automatically determine which data points/datasets to further process or an operator may partially or fully make such a determination. A dataset may include process variables or system parameters such as oxidation-reduction potential, pH, levels of certain chemicals or ions (e.g., determined empirically, automatically, fluorescently, electrochemically, colorimetrically, measured directly, calculated), temperature, pressure, process stream flow rate, dissolved or suspended solids, etc. Such system parameters or process variables are typically measured with any type of suitable data capturing equipment, such as pH sensors, ion analyzers, temperature sensors, thermocouples, pressure sensors, corrosion probes, and/or any other suitable device or method. Data capturing equipment is preferably in communication with the controller and, according to alternative embodiments, may have advanced functions (including any part of the control algorithms described herein) imparted by the controller.

Data transmission of measured parameters or signals to chemical pumps, alarms, or other system components is accomplished using any suitable device, such as a wired or wireless network, cable, digital subscriber line, internet, etc. Any suitable interface standard(s), such as an ethernet interface, wireless interface (e.g., IEEE 802.11a/b/g/x, 802.16, Bluetooth, optical, infrared, radiofrequency, etc.), universal serial bus, telephone network, the like, and combinations of such interfaces/connections may be used. As used herein, the term "network" encompasses all of these data transmission methods. Any of the described devices (e.g., plant archiving system, data analysis station, data capture device, process station, etc.) may be connected to one another using the above-described or other suitable interface or connection.

In at least one embodiment, system parameter information is received from the system and archived. In another embodiment, system parameter information is processed according to a timetable or schedule. In a further embodiment, system parameter information is immediately processed in real-time/substantially real-time. Such real-time reception may include, for example, "streaming data" over a computer network.

In at least one embodiment two or more samples are taken at different locations in the system. For example one could be at the dew point and one at the boot accumulator. The measurement differences at these two sample points require a corresponding algorithm to adjust chemical injection. The term "dew point" refers to the point of initial condensation of steam to water or the temperature at which a phase of liquid water separates from the water vapors and liquid hydrocarbons and begins to form liquid water as the vapors cool. Though possible to use the accumulator water boot to measure pH and chloride ion level, a level of accuracy is usually sacrificed because data is diluted or masked by the full volume of steam and weak acids and bases that have condensed downstream of the water dew point.

Likewise, it is possible to measure iron (or other metals, such as copper, molybdenum, nickel, zinc) ion concentration from the dew point water. In at least one embodiment the metal ion concentration is measured at the accumulator water boot because these ions indicate corrosion has taken place and metal has been removed from an internal component in the system upstream of the sample point.

It should be appreciated that any suitable method may be used for obtaining the dew point water sample. For example, devices for obtaining the dew point water sample are disclosed in U.S. Pat. No. 4,335,072, titled "Overhead Corrosion Simulator" and U.S. Pat. No. 5,425,267, titled "Corrosion Simulator and Method for Simulating Corrosion Activity of a Process Stream," each of which is incorporated herein by reference in its entirety.

In at least one embodiment, different fluid or system parameters or process variables or other constituents present in the system could be measured and/or analyzed including but not limited to pH; chloride ion; other strong and weak acids, such as sulfuric, sulfurous, thiosulfurous, carbon dioxide, hydrogen sulfide; organic acids; ammonia; various amines; and liquid or solid deposits and the like. Various methods of taking measurements are contemplated and the invention is not limited to one particular method. Representative methods include, but are not limited to those disclosed in U.S. Pat. Nos. 5,326,482, 5,324,665, and 5,302,253.

In response to the measurements taken at various locations in the system remedial chemistry can be added to the system to respond to the measured readings. Such remedial chemistries include but are not limited to neutralizers, filming inhibitors (sometimes referred to herein as "filmers"), and caustic agents. These points are labeled "Neutralizer based on acid or pH," "Filmer based on iron," and "Caustic based on chloride." It should be appreciated that such chemicals may be added at any suitable location in the system. In at least one embodiment, introduction of such chemicals into the system are adjusted continuously. In other embodiments, chemical introduction is adjusted intermittently or in relation to a schedule as determined for each individual system.

Neutralizer(s), caustic agent(s), and filming inhibitor(s) may be introduced to the system using any suitable type of chemical feed pump. Most commonly, positive displacement injection pumps are used powered either electrically or pneumatically. Continuous flow injection pumps are sometimes used to ensure specialty chemicals are adequately and accurately injected into the rapidly moving process stream. Though any suitable pump or delivery system may be used, exemplary pumps and pumping methods include those disclosed in U.S. Pat. No. 5,066,199, titled "Method for Injecting Treatment Chemicals Using a Constant Flow Positive Displacement Pumping Apparatus" and U.S. Pat. No. 5,195,879, titled "Improved Method for Injecting Treatment Chemicals Using a Constant Flow Positive Displacement Pumping Apparatus," each incorporated herein by reference in its entirety.

Representative neutralizers include but are not limited to 3-methoxypropylamine (MOPA) (CAS #5332-73-0), monoethanolamine (MEA) (CAS #141-43-5), N,N-dimethylaminoethanol (DMEA) (CAS #108-01-0), and methoxyisopropylamine (MIOPA) (CAS #37143-54-7).

As a caustic agent, a dilute solution of sodium hydroxide is typically prepared in a 5 to 10% concentration (7.5 to 14° Baume) for ease of handling and to enhance distribution once injected into the crude oil, or desalter wash water, for example. Concentration may be adjusted according to ambient conditions, such as for freeze point in cold climates.

Filming inhibitors or filmers used in conjunction with this invention in a crude unit corrosion control program are typically oil soluble blends of amides and imidazolines. These compounds offer good corrosion control with minimal effects on the ability of the hydrocarbons in the system to carry water.

It should be appreciated that a suitable pH control or optimal range should be determined for each individual system. The optimum range for one system may vary considerably from that for another system. It is within the concept of the invention to cover any possible optimum pH range.

In different embodiments, changes in the neutralizer pump are limited in frequency. Preferably, adjustment limits are set at a maximum of 1 per 15 min and sequential adjustments in the same direction should not exceed 8. For example, after 8 total adjustments or a change of 50% or 100%, the pump could be suspended for an amount of time (e.g., 2 or 4 hours) and alarm could be triggered. If such a situation is encountered, it is advantageous to trigger an alarm to alert an operator. Other limits, such as maximum pump output may also be implemented. It should be appreciated that it is within the scope of the invention to cause any number of adjustments in any direction without limitation. Such limits are applied as determined by the operator.

It should be appreciated that a suitable or optimal chloride ion concentration range should be determined for each individual system. The optimum range for one system may vary considerably from that for another system. It is within the concept of the invention to cover any possible optimum chloride ion concentration range.

In at least one embodiment other metallurgy is used so such as monel, titanium, brass, etc. may be used in some systems. In these cases, rather than an iron ion concentration signal, the appropriate metal ion (e.g., copper, nickel, zinc, etc.) concentration signal would be detected and analyzed.

Metal ions commonly exist in two or more oxidation states. For example, iron exists in $Fe^{2+}$ and $Fe^{3+}$ as well being present in soluble states (ionic and fine particulate), insoluble states (i.e., filterable), etc. Analysis and control of metal ions includes measurement or prediction of any combination (or all) of such permutations present in the system.

Although the corrosion probes (e.g., electrical resistance corrosion probes, linear polarization probes, and/or any other suitable method for determining metal loss) may be placed at any convenient location in the system, preferably they are placed in historically reliable locations in the system. In addition, if, for example, 2 overrides are activated over a 12 hr period, a reliability check is typically initiated to ensure that the corrosion probes are operating properly. If such a situation is encountered, it is advantageous to trigger an alarm to alert an operator. Other limits, such as maximum pump output may also be implemented. It should be appreciated that it is within the scope of the invention to cause any number of adjustments in any direction without limitation. Such limits are applied as determined by the operator.

In at least one embodiment, if the communication link between the analyzer and the controller is severed or impaired, the controller continues with whatever action it was undertaking prior to losing communication. In at least one embodiment, if the communication link between the analyzer and the sensor is severed or impaired the controller continues with whatever action it was undertaking prior to losing communication. In at least one embodiment, if the analyzer output induces the controller to enact a response beyond the physical limitations of the equipment, the controller the best response possible (such as turning on/off one or more pumps, vents, drains, lifts, stators, conveyers, furnaces, heat exchangers . . . etc.) and the controller keeps that underperforming responding equipment running at its maximum capacity until the analyzer output warrants a reduction. In at least one embodiment at least one piece of responding equipment is constructed and arranged to respond to analyzer output only gradually. In at least one embodiment while the equipment can respond only gradually, it is constructed and arranged to return to its pre-response setting as soon as physically possible. This allows for the negation of an incorrect response before the response has caused a significant effect. An example of gradual response is a pump that increases the flow of chemical from 0% of a maximum flow rate to 100% of maximum flow rate over the course of up to 10 minutes even though it can reach 100% within a few seconds.

In at least one embodiment the analyzer utilizes a model method of data analysis to correct for inaccuracies that occur in the measurements of process variables. Because corrosion is by definition the result of a finite amount of mass from the plant equipment detaching from those pieces of equipment, the amount of corrosion measured should be easy to correlate with physical damage to components of the system. However due to large amounts of noise inherent in such facilities the measured rates, fluctuate widely and are often not accurate. Significantly the noise often leads to measured corrosion rates greater than the actual mass that has been removed from the equipment. In addition different forms of crude oil (especially opportunity crude) and inconsistencies in their composition cause equipment to often function differently during different production runs. This leads to varying and hard to predict rates of corrosion. Moreover as corrosion changes the very environment being analyzed each production run may make further ambiguous future analyses.

Figure 1:
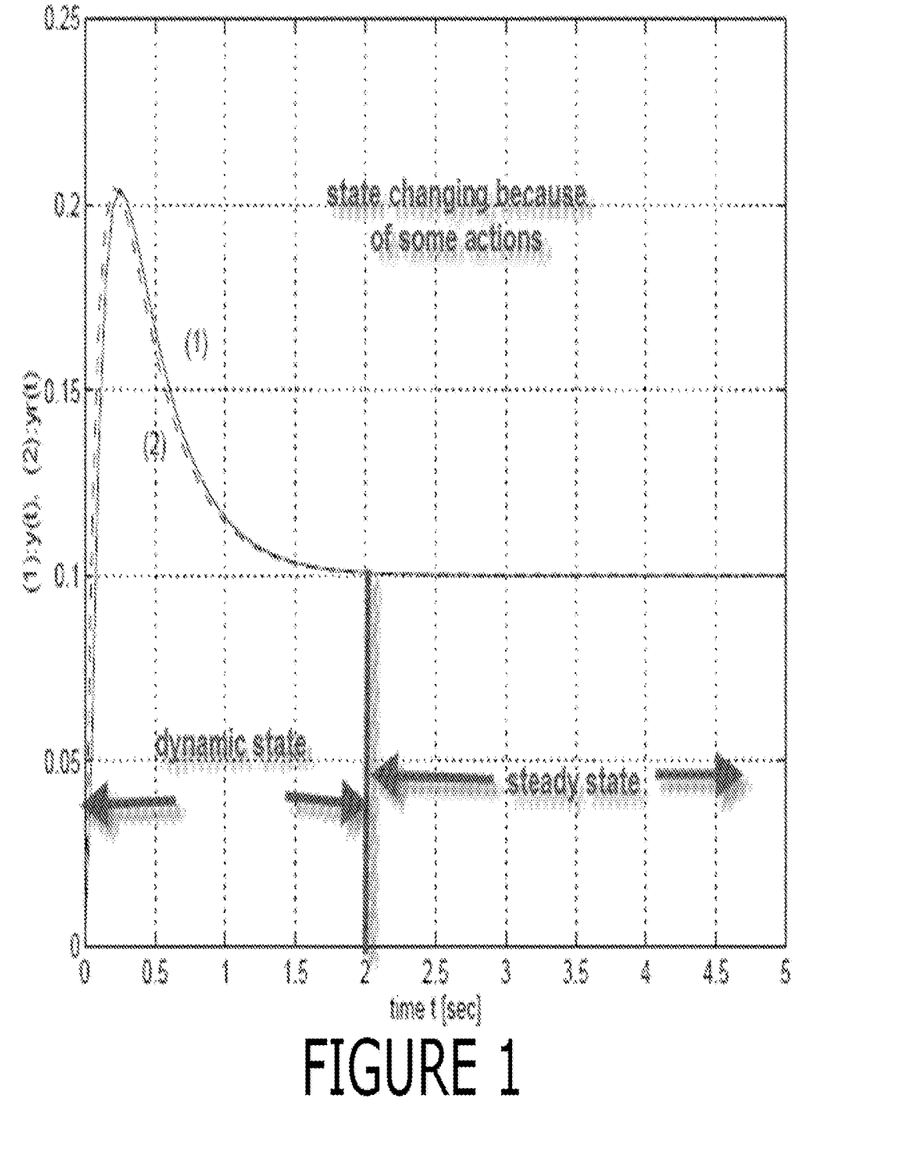
FIG. 1 is a graph which illustrates a method of correcting a measured value of a process variable.
Figure 2:
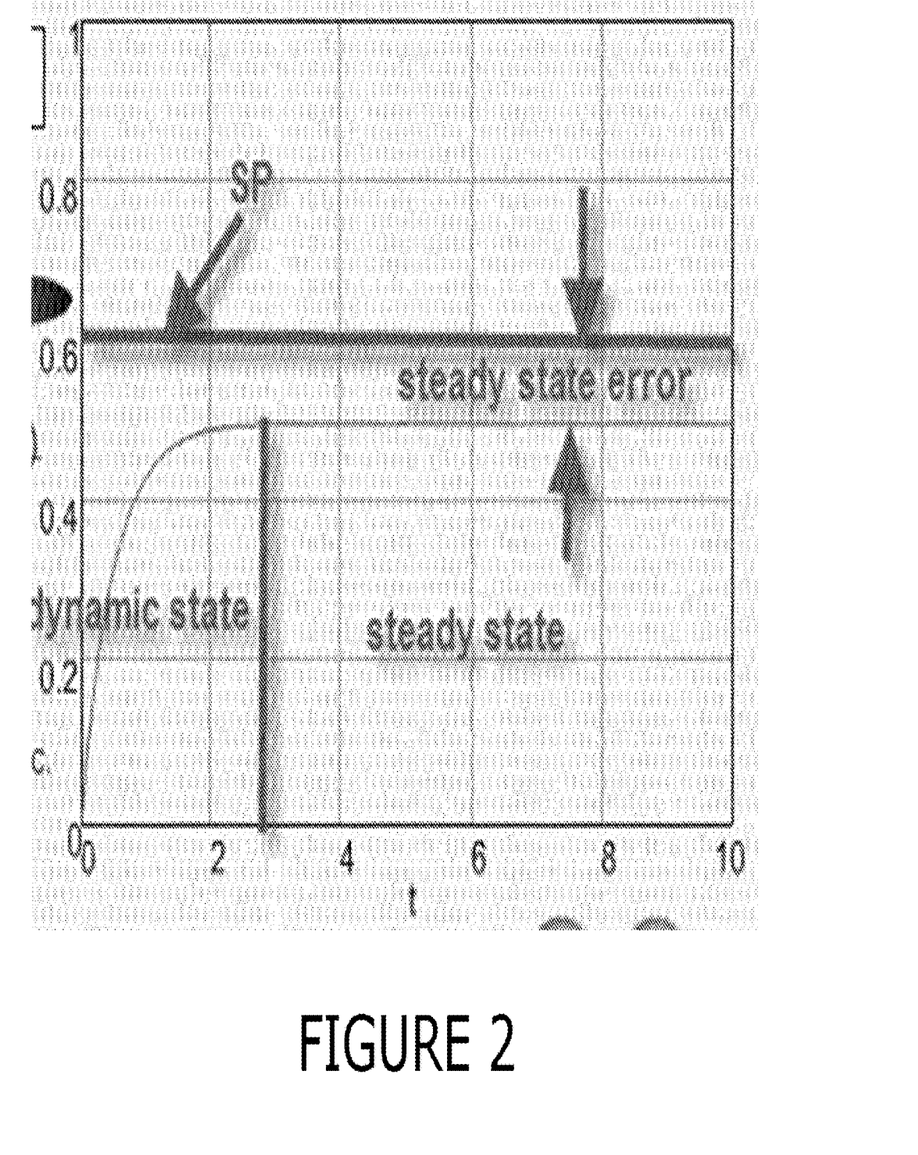
FIG. 2 is a graph which illustrates a method of correcting a measured value of a process variable.

In at least one embodiment the analysis takes into account the known difference between the steady state measurement and the dynamic state measurement taken by the sensor to correct for inaccuracies that occur in the measurements of process variables. As illustrated in FIG. 1, in many situations a disturbance in the system (such as turning on or off a pump, adding or ceasing addition of a chemical, changing pH, [Fe], temperature, pressure, etc . . . ) causes a short term dynamic state change in the sensor measurement as well as a longer term steady state change in the sensor measurement.

The analyzer learns to associate the specific dynamic state changes that occur in response to specific disturbances with specific sensors and when under those conditions it detects a similar dynamic measurement, instead of outputting the detected measurement the analyzer outputs the corrected value that it has learned is associated with the properties of the detected dynamic state.

As a result, in at least one embodiment the output of at least one sensor measurement of a process variable obtained by the analyzer undergoes a conversion. That output can be represented by the function:

$$u=f(e,\Delta e,d)$$

in which u is output of the analyzer measuring a process variable, e is the error detected in the dynamic state, d is the magnitude of the disturbance that caused the error, and $\Delta e$ is the change in the error over time. The error itself can be calculated using the equation:

$$e=SP-PV$$

in which PV is a process variable, or the actual value that the analyzer measured for the variable and SP is the setpoint or what the value should have been but for the disturbance based noise.

In at least one embodiment the specific parameters of any predictive function used to correct for a measured process variable can be calculated through direct observation of the system.

Utilizing the above equations, one of ordinary skill in the art would recognize that based on a Taylor series expansion, $$\begin{aligned}u &= f(e,\Delta e, d) \\ &\approx f(e^0,\Delta e^0, d^0) + \frac{\partial f}{\partial e}\bigg|_{e=e^0}(e-e^0) + \frac{\partial f}{\partial \Delta e}\bigg|_{\Delta e=\Delta e^0}(\Delta e - \Delta e^0) + \\ &\quad \frac{\partial f}{\partial d}\bigg|_{d=d^0}(d-d^0) + \Delta \\ &= u^0 + f(e) + f(\Delta e) + f(d) + \Delta\end{aligned}$$

where $u^0$ denotes steady state controller output; $e^0$, $\Delta e^0$, and $d^0$ are e, $\Delta e$ and d. The controller consists of two parts: steady state, $u^0=f(e^0, \Delta e^0, d^0)$ and dynamics $f(e)$, $f(\Delta e)$, $f(d)$. The steady state can be obtained from direct measurements of the system steady state. In at least one embodiment at steady state at least one of $e^0$, $\Delta e^0$, and $d^0$ are e, $\Delta e$ and d is 0.

The dynamic part is approximated by the following nonlinear dynamic model:

$\Delta$ represents lumped uncertainties and other unmodeled terms. In at least one embodiment it can be attenuated by control technology because it is bounded.

At steady state, $u^0$ is known by human experience, or it is easy to know by test or simple analysis and modeling. One useful meaning of $u^0$ is the result of the ideal pump output when the controlled variable is at its target. Each dynamic part $f$ is a tunable function based on specific process, the function is also knowledge based and within a control limits $[u_{min}, u_{max}]$. In at least one embodiment the function is designed according to a proportional format. In at least one embodiment the function is designed according to a sigmoid format.

In at least one embodiment the system comprises output limits and the variable limits $[PV_{min}, PV_{max}]$ to designate the boundaries permissible by system control. In practice, $u_{min}=u^0-U_c$; $u_{max}=u^0+U_c$; $PV_{min}=SP-SP_c$; $PV_{max}=SP+SP_c$;

where $U_c$ is a output scale factor which is a constant tuned on-line, $SP_c$ is the variable scale factor which is a constant tuned on-line.

In addition, the resulting changes in the system due to feeding chemicals needs to be predictable. Precise control of pH and corrosion is quite difficult due to large variations in process dynamics. One difficulty arises from the static nonlinear relationship in results of chemical additions such as titration. Titration is the relationship between pH of a medium and the concentration of acids and bases in that medium. The nonlinearity in titration depends on the substances in the solution and their concentrations. For example the presence of some weak acids or weak bases causes a buffering effect (a resistance to proportional changes in pH despite proportional changes in the concentrations of acids and bases).

Other chemistries present in the process system may also have non-linear responses to added chemicals. In addition because of the ebb and flow rate of operations in a process system, there are very long periods of deadtime. As previously mentioned $u^0$ can be represented by the result of the ideal pump output when the controlled variable is at its target. In practice however due to sizes, distances that the chemicals must traverse, and other physical constraints, the pump is in fact not ideal and there is a significant lag between when the instruction is given to feed a chemical, and when the chemical appears in the system in a dosage significant enough to appropriately affect the system. For purposes of this application, the time lag between activating a pump and the pump causing the proper effect is known as "deadtime." During deadtime a number of changing dynamics occur which lead to wildly inaccurate measurements of process variables.

In at least one embodiment the analyzer utilizes a combination of human knowledge and experience to adjust feed rates to take into account the nonlinear properties the controller must address. This makes the controller more intelligent and feasible.

The presence of other materials in the process system often affects the nature of various acids further complicating any attempt to predict resulting pH from changing the concentrations. As a result, if graphed, the shape of the expected titration curve becomes quite irregular. In at least one embodiment, by disregarding noise and error, the analyzer can accurately model and predict the correct titration curves is required for effective pH control.

As a result, a method of signal processing may need to be utilized to correctly measure a process variable. Suitable forms of signal processing include but are not limited to DSP algorithms, filtering (including low pass, high pass, adaptive, and moving average filters), smoothing, ARX, Fourier transform, S-plane analysis, Z-plane analysis, Laplace transforms, DWT, wavelet transforms, bilinear transforms, and Goertzel algorithms. In at least one embodiment analysis using dynamic state error is done prior to the signal processing. In at least one embodiment analysis using dynamic state error is subsequent to the signal processing.

Signal processing is of particular benefit with regards to detecting Fe. One particular error involves the trend of iron detection to drop to zero. This reading is obviously erroneous. As a result, if the signal processing does not correct for zero concentration of Fe in a system that obviously contains Fe due to ongoing or previous corrosion, the analyzer will correct the iron reading to what its learned experience indicates it should be and/or to what the reading was immediately before it began its drop to zero. In at least one embodiment, if the sensor detects zero iron the analyzer does not pass on the detected iron value to the controller but instead passes on a value based on what the iron level should be based on previous performance under similar conditions.

In at least one embodiment the control system comprises one or more methods, compositions, and/or apparatuses described in Published U.S. Patent Application 2012/0053861 A1.

In at least one embodiment the control system comprises one or more redundant sensors detecting the same process variable at substantially the same location in the process system. Because much of the noise causing inaccuracies is random in nature, the errors do not always affect all the sensors at the same time. As a result under certain circumstances a minority of sensors may be erroneous and a majority may be correct. In at least one embodiment if all of the sensors provide readings consistent with pre-determined setpoints based on the specific conditions present, the analyzer returns the average measurement to the controller. In at least one embodiment if at least one of the sensors provides measurements consistent with the setpoints, the analyzer returns the average measurement of the consistent measurements to the controller. In at least one embodiment if all of the sensors provide measurements inconsistent with the setpoints, the analyzer rejects all of the measurements and instead passes on to the controller measurements based on historical data until at least one sensor again provides consistent measurements. In at least one embodiment the historical data will be the average of some or all previous measurements consistent with the setpoints.

In at least one embodiment, the analyzer's variable sampling period is much longer than that of normal transmitters, (in some cases as high as 60 minutes). In addition, the controlled variable expectations (setpoints) are normally in a range instead of a single point.

In at least one embodiment remedial chemistry or process chemistry fed by the controller is added according to a feedforward model. Feedforward can best be understood by contrasting it to a feedback approach. In feedback the receipt of information about a past event or condition influences the same event or condition in the present or future. As a result the chain of cause and effect forms a circuit loop that feeds back into itself.

In a feedforward model the reaction to the information occurs before the actual information is received. This allows for faster reaction to system problems, reducing the duration, severity, and consequences of unwanted conditions. Feedforward can be achieved using the same observations that are used to determine the analyzer output function. Specifically because the analyzer changes the output to the correct value before the correct value is detected by the sensor (in some cases while it is still receiving dynamic state changing information.) Moreover feedforward allows for the elimination of conditions that would otherwise persist during the deadtime between the actual existence of an unwanted condition and the delays caused by inaccurate measurements and imperfect pump flow properties. In at least one embodiment the feedforward strategy addresses an unwanted system condition faster than a feedback system can.

In at least one embodiment the feedforward model is used to analyze the variable relationship and eliminate the interactions. For example, in a crude oil refinery logic used to determine if corrosion control measures needs to be enacted in response to Fe concentration would be governed by a feedforward model reacting to analyzer output according to a function of (Caustic, Neutralizer). This control algorithm provides whole functionalities and capabilities to implement feedforward model. In at least one embodiment the properties of the feedforward strategy is included in the controller algorithm. The format of the controller algorithm its data analysis can be designed based on specific properties of the system it is used within.

As previously mentioned because corrosion is due to loss of mass in process equipment, by definition the detected amounts of corrosion should equal the lost mass. Because that however is not what the sensors often detect, special measures need to be taken by the analyzer to correct the detected levels of corrosion. In at least one embodiment the corrosion rate (CR) is corrected by the analyzer by taking into account both on-line detected levels and an analysis of the corrosion rate.

In at least one embodiment this analysis makes use of two definitions of CR, instant CR and period CR. Both of the two rates reflect different aspects of corrosion speed. Instant CR is defined as the rate of metal loss change at a specific fixed period of time, e.g. one day or week. In at least one embodiment a corrosion probe (the sensor) is used to detect a raw value. Due to the noisy signal inherent in such detections, a linear regression or other form of signal processing may be used to correct the detected value of Instant CR. Instant CR provides insight into instantaneous causes of corrosion which is extremely helpful in determining the effect of changes in the process system conditions.

Figure 3:
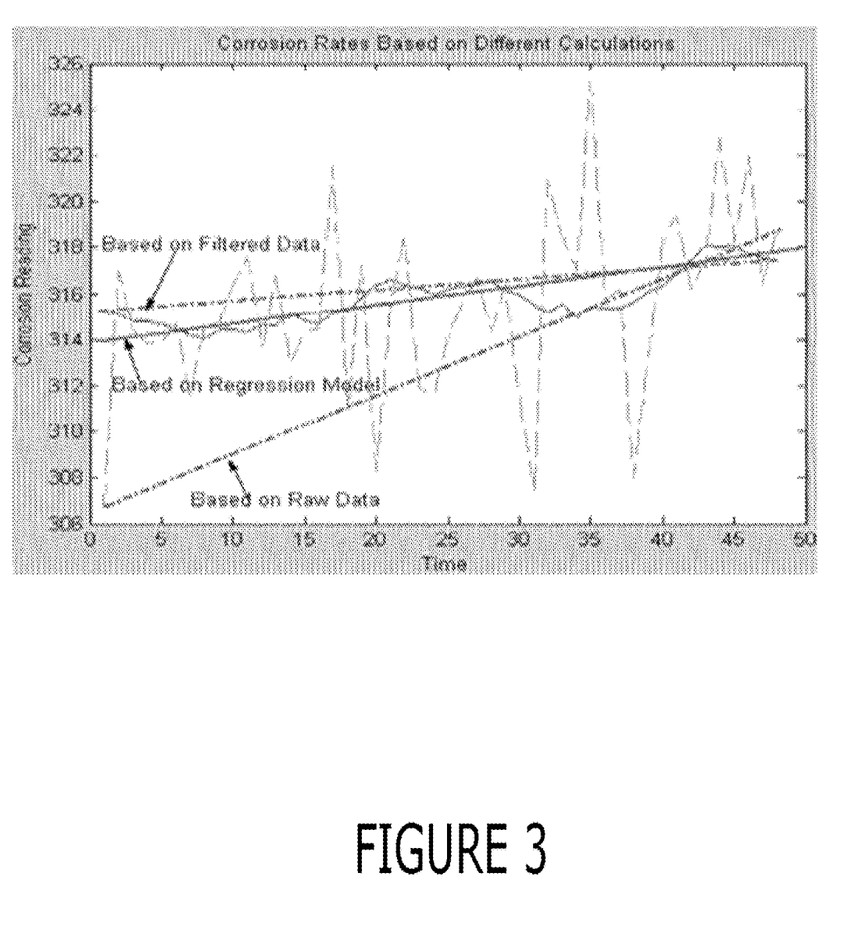
FIG. 3 is a graph illustrating the difficulty in calculating the corrosion rate of a process system.
Figure 4:
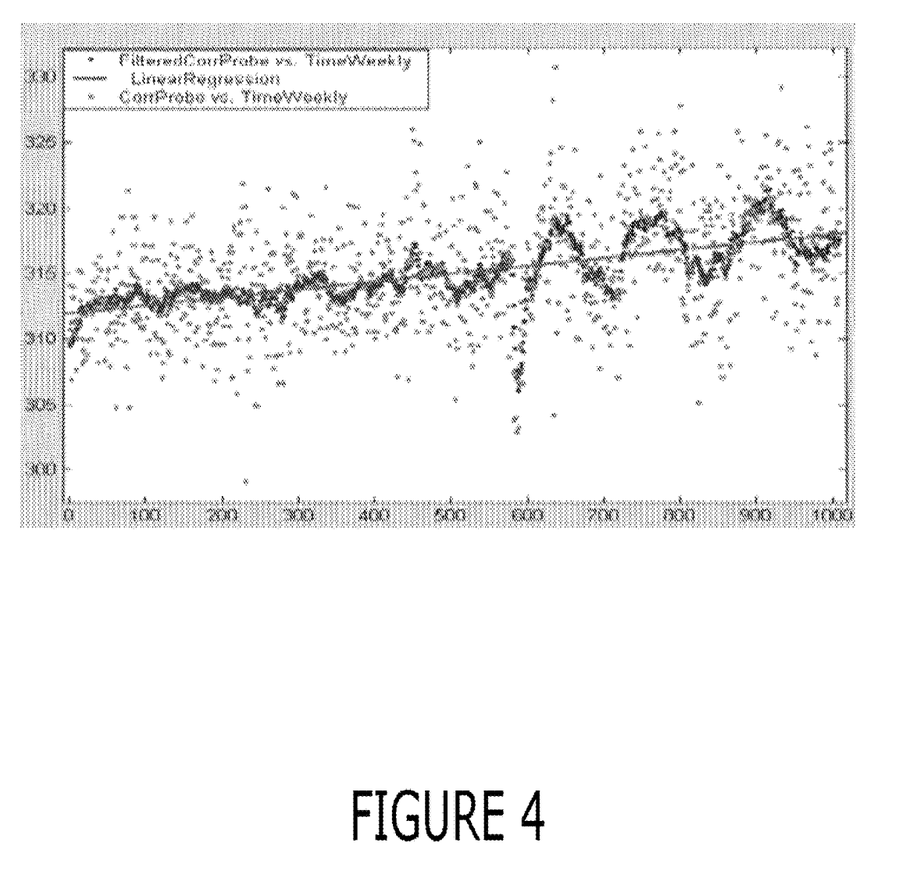
FIG. 4 is a graph which illustrates a method of correcting a measured value of corrosion rate.

In at least one embodiment Period CR requires several days or weeks to determine the general corrosion rate. Period CR is determined by identifying which linear function best represents the metal loss in such noisy environment. A simple linear calculation is based on two points of beginning and end, this calculation assumes the metal loss is monopoly increased function, does not consider the data between the two points. Obviously, this calculation does not reflect real situation under noisy signals, most likely, this calculation is far away from reality. A proper linear curve is generated by least squares regression, which minimize the total distances between each point to the linear curve.

$$\min \Sigma(y-Y_i)^2$$

where Y represents the linear curve we design; Yi denotes real probe reading at i point. FIGS. 3 and 4 show compared corrosion rates based on two point corrosion reading, two point filtered corrosion reading, and linear regression. Essentially, the corrosion rate is the slope of the linear curve, it shows how big discrepancy of the three calculations, and also we can understand which calculation is more reasonable and scientific. As shown in FIG. 3, using a linear analysis of detected corrosion rates over the period can result in multiple rates based on which form of analysis is used.

As illustrated in FIG. 4, in at least one embodiment the use of the linear representation of the average regression curve is used to identify the actual rate of corrosion that occurs in the system.

In at least one embodiment the decision regarding which linear representation to use is constantly updated to best reflect observations made of the system.

Figure 5:
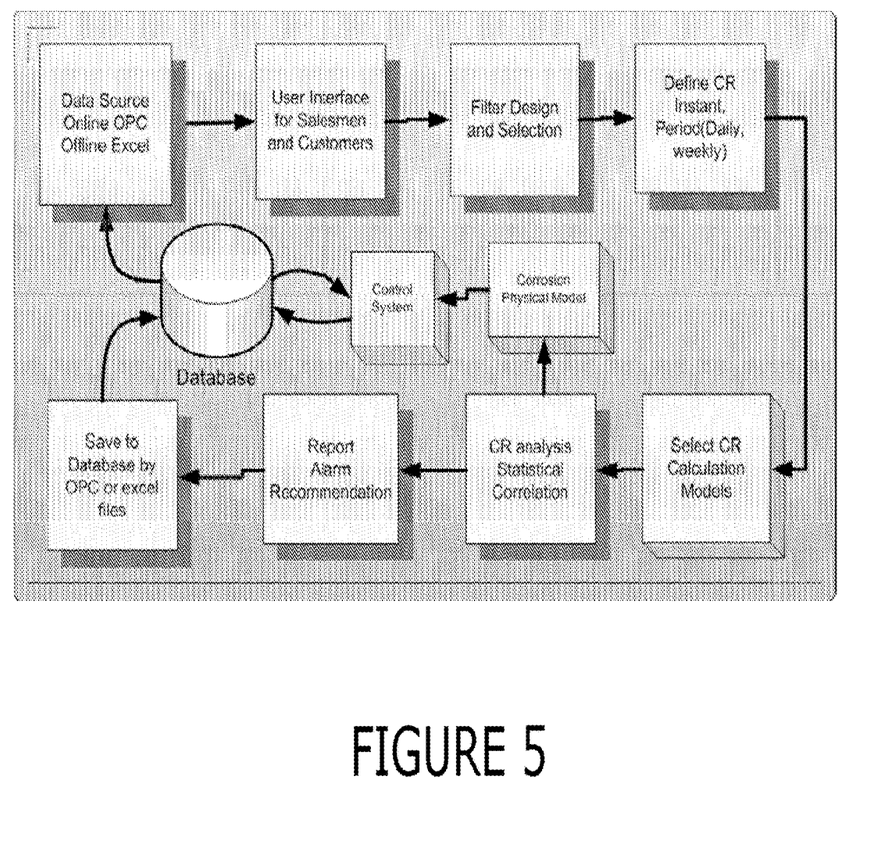
FIG. 5 is an illustration of sources of data used by the analyzer.

Referring now to FIG. 5 there is shown a logical flowchart illustrating how information from various sources is constantly fed to and used by the analyzer to improve the logic it uses to correct for incorrect readings. The analyzer utilizes:

(1) On-line and off-line filter design to smooth noisy corrosion probe reading and exclude outliers, (2) corrected definitions of corrosion rates (instant running rate, period rate) and their relationship to each other. This gives different definitions to calculate and compare. (3) On-line (running regression CR) and off-line corrosion rate calculation and monitoring and alarming corrosion rate. (4) Corrosion rate evaluation and analysis, used by the controller, and (5) automatically generated analysis reports.

In at least one embodiment the control system makes use of on-line measurements of Process changes in one or more of temperature, pressure, velocity and concentration to detect acceleration in corrosion rate. This can be done by making use of instant CR and period CR.

In at least one embodiment the analysis is according to the following equations: Instant CR=dy/dt. Therefore:

$$\text{Instant } CR = \frac{dy}{dt} = \lim_{\Delta t \to 0} \frac{\Delta y}{\Delta t}$$

Because Period CR can be said to be the rate of metal loss change at a fixed period of time, such as $\Delta t$ or $\Delta y/\Delta t$. However, because of the signal "noise" that accompanies metal loss y, if a linear regression of y is first used and then Period CR is calculated as the slope with time $\Delta t$ then:

$$\text{Period } CR = \frac{\Delta y}{\Delta t}$$

Instant CR and Period CR reflect different aspects of corrosion speeds. In at least one embodiment Period CR is determined over several days or weeks to determine the general corrosion rate; Instant CR is instantaneous corrosion which is extremely helpful in determining the effects of process changes on corrosion.

In at least one embodiment the relationship between Instant CR and Period CR is determined by an integral mean-value theorem. For example:

$$\text{Period } CR = \frac{\Delta y}{\Delta t} = \frac{y_{t2} - y_{t1}}{t2 - t1} = \frac{\int_{t1}^{t2} \frac{dy}{dt} dt}{t2 - t1} = \frac{\frac{dy}{dt}|_\xi (t2 - t1)}{t2 - t1} = \frac{dy}{dt}|_\xi$$

In which there exist a point $\xi$ in [t1, t2] where the instant CR will be the same as the Period CR. This point however will not necessarily be the mean, median, mode, and/or average of Instant and Period CR.

Although the corrosion process is very complex, under certain circumstances the corrosion rate can approximate a simple linear function of time t, according to the equation: y=at+b where y is the monopoly metal loss function; t is time, and a and b denote the slop and bias of the function. Both a and b are all time-invariant constants.

Under this approximation:

$$\text{Instant } CR = \frac{\partial y}{\partial t} = a = \frac{\Delta y}{\Delta t} = \frac{y - y_0}{t - t_0} = \text{Period } CR$$

This illustrates that if and only if the slope and bias a, b are unchanged constants in the period of time $\Delta t$ then Period CR will be equal to Instant CR.

Figure 6:
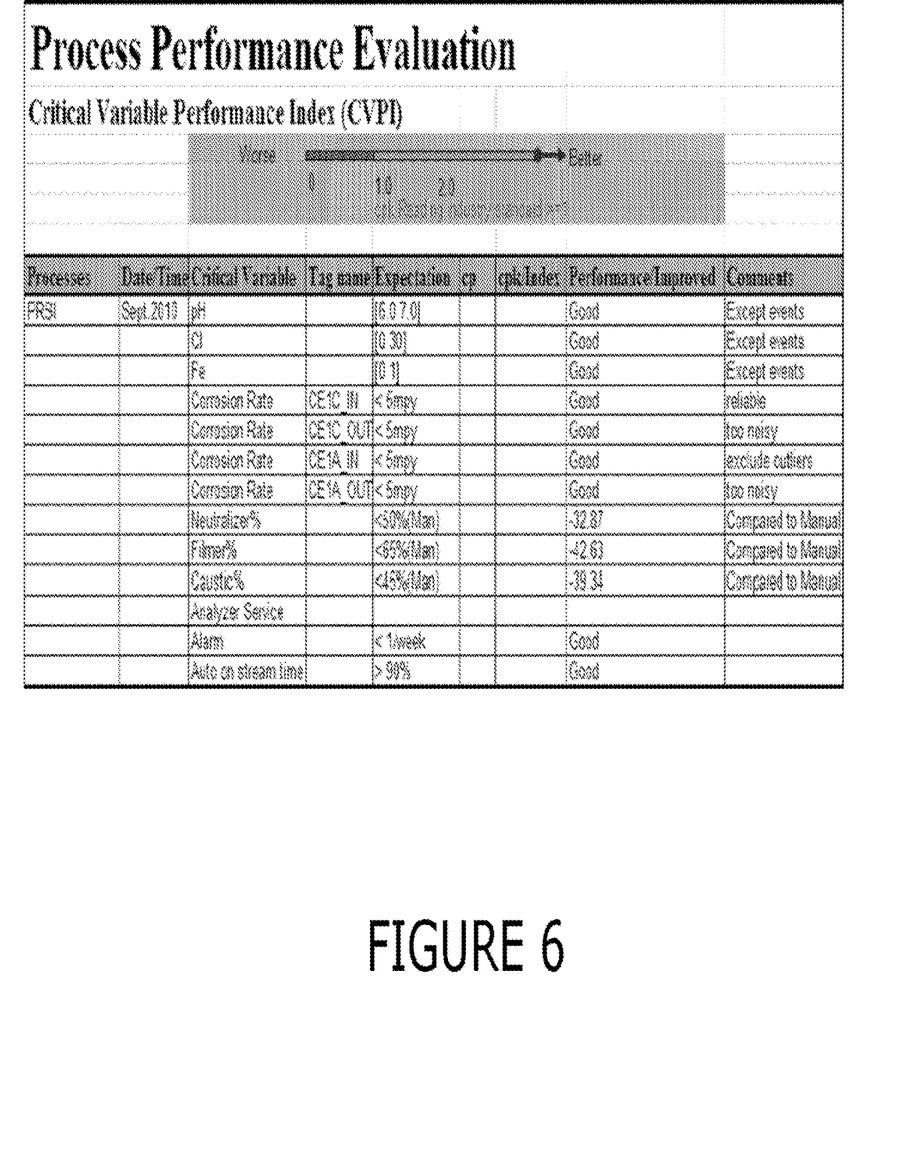
FIG. 6 is an illustration of a dashboard containing analyzer output.

As shown in FIG. 6, in at least one embodiment the analyzer outputs information into a dashboard format that provides a user with a helpful and easy to understand perspective on the operations of at least a portion of the system. For example the various detected performance variables can be expressed according to a relative evaluation indicating how well or poor the system is doing.

In at least one embodiment the evaluation will be expressed according to at least one of the following categories:

Control Variable Stability
  Variable stability is very critical for process operation. In crude unit corrosion control system, three critical variables (pH, Cl, Fe) are the key to maintain the corrosion system stable. Daily cpk is used and compared.

Chemical Usage
  Neutralizer, Caustic and Filmer are used to control the three controlled variables, pH, Cl and Fe. One of objectives of this control design is to maintain the controlled variables while saving the chemical usages.

Evaluation on Automation System Operation
  The system not only provides the key variable measurement by the analyzer, but also (1) The system provides whole information, include pumps, boot water pressures, working temperatures, inferred chemical flow rates, corrosion . . . (2) Provides friendly interface, gives us a platform to remotely monitor and operate the whole system, modify parameters . . . (3) Collects analyzer alarms, generates/sets all variable operation alarms, and provides instant cell phone and email alarms, (4) Provides a platform of on-line and off-line data analysis and translating information into refined knowledge . . . , this is the spotlight of the system, (5) The control system on stream time is 100% except some events happened.

Corrosion Performance Analysis
  On line corrosion rate must be calculated and compared with other variables. FIG. 7 gives an example of a weekly period corrosion rate based on two probes. FIG. 8 shows an evaluation demonstrating that the corrosion rate is strongly correlated to the critical variables Fe and pH.

In at least one embodiment the process system that the control system in used within contains at least one of a crude unit, de-salter, atmospheric tower, vacuum tower, cooling unit, heating unit, furnace, cracker, and any combination thereof. The control system will optimize and improve the performance of some, part or all the components of the process system. Such improvement will (1) Improve and maintain process stability and reliability. (2) Optimize chemical usages and reduce cost. (3) Improve system robustness, operating flexibility, provide reliable information system and friendly low-cost interface. (4) Define, calculate, monitor, control and optimize corrosion rate.

In at least one embodiment, not only does the control system determine and predict the corrosion in the aqueous phase of a crude unit overhead system but it can also calculate and predict the formation of salts as well as their impact of corrosion. In at least one embodiment, the analyzer can calculate in real time the amount of additive (amine) to inject to remedy the impact of salts on corrosion.

In at least one embodiment this calculation is achieved by using at least one of the following inputs: pH, chloride, temperature, pressure, density, flowrate, wash water rate, total steam, and the presence of the following compounds: Chloride, total amine, total nitrogen, halogen, bromide, iodide, oxygen, water, and ammonia level. In at least one embodiment this is accomplished by the addition of and observation of the reaction of one or more of the following amines: methylamine, dimethylamine, trimethylamine, ethylamine, diethylamine, triethylamine, n-propylamine, isopropylamine, di-n-propylamine, di-isopropylamine, n-butylamine, sec-butylamine, 1-amino-2,2-dimethylpropane, 2-amino-2-methylbutane, 2-aminopentane, 3-aminopentane, morpholine, monoethanolamine, ethylenediamine, propylenediamine, N,N-dimethylethanolamine, N,N-diethylethanolamine, N,N-dimethylisopropanolamine, Methoxyethylamine, Piperidine, Piperazine, Cyclohexylamine, N-methylethanolamine, N-propylethanolamine, N-ethylethanolamine, N,N-dimethylaminoethoxyethanol, N,N-diethylaminoethoxyethanol, N-methyldiethanolamine, N-propyldiethanolamine, N-ethyldiethanolamine, t-butylethanolamine, t-butyldiethanolamine, 2-(2-aminoethoxy)ethanol, di-n-butylamine, tri-n-butylamine, di-iso-butylamine, ethyl-n-butylamine, pentylamine, 2-amino-2,3-dimethylbutane, 3-amino-2,2-dimethylbutane, 2-amino-1-methoxypropane, dipropylamine, monoamylamine, n-butylamine, isobutylamine, 3-amino-1-methoxypropane, and any combination thereof.

Using sensors to detect pH, Chloride, Fe, as well as at least one nitrogen sensor, at least one total nitrogen sensor or the combination thereof, a mathematical model can calculate the formation of salt and or corrosive species. This information and the corresponding calculations can be made in real time from a sample collected in real time. The calculated and stored information can then be used to calculate and control the addition of additives in real time into the overhead based on the corrosive nature and composition of the compounds present in the overhead.

In at least one embodiment the control system can continuously recalculate in real time the corrosive conditions; the salt formation and have the controller add appropriate additives should any one-parameter change. These additives include but are not limited to: Water, Sodium Hydroxide, potassium hydroxide, lithium hydroxide, methylamine, dimethylamine, trimethylamine, ethylamine, diethylamine, triethylamine, n-propylamine, isopropylamine, di-n-propylamine, di-isopropylamine, n-butylamine, sec-butylamine, 1-amino-2,2-dimethylpropane, 2-amino-2-methylbutane, 2-aminopentane, 3-aminopentane, morpholine, monoethanolamine, ethylenediamine, propylenediamine, N,N-dimethylethanolamine, N,N-diethylethanolamine, N,N-dimethylisopropanolamine, Methoxyethylamine, Piperidine, Piperazine, Cyclohexylamine, N-methylethanolamine, N-propylethanolamine, N-ethylethanolamine, N,N-dimethylaminoethoxyethanol, N,N-diethylaminoethoxyethanol, N-methyldiethanolamine, N-propyldiethanolamine, N-ethyldiethanolamine, t-butylethanolamine, t-butyldiethanolamine, 2-(2-aminoethoxy)ethanol, di-n-butylamine, tri-n-butylamine, di-iso-butylamine, ethyl-n-butylamine, pentylamine, 2-amino-2,3-dimethylbutane, 3-amino-2,2-dimethylbutane, 2-amino-1-methoxypropane, dipropylamine, monoamylamine, n-butylamine, isobutylamine, 3-amino-1-methoxypropane, and any combination thereof.

In at least one embodiment the control system can detect through the use of sensors the corrosion resulting from aqueous fluids or the formation of salt compounds. These sensors are pH, Chloride, Fe, Nitrogen, total nitrogen, ammonia, electrical resistance corrosion probes. In addition to measuring the corrosive environment these sensors provide input into the analyzer facilitating the calculation of appropriate amounts of chemical additives.

While this invention may be embodied in many different forms, there described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments described herein and/or incorporated herein. In addition the invention encompasses any possible combination that also specifically excludes any one or some of the various embodiments described herein and/or incorporated herein.

The above disclosure is intended to be illustrative and not exhaustive. This description will suggest many variations and alternatives to one of ordinary skill in this art. The compositions and methods disclosed herein may comprise, consist of, or consist essentially of the listed components, or steps. As used herein the term "comprising" means "including, but not limited to". As used herein the term "consisting essentially of" refers to a composition or method that includes the disclosed components or steps, and any other components or steps that do not materially affect the novel and basic characteristics of the compositions or methods. For example, compositions that consist essentially of listed ingredients do not contain additional ingredients that would affect the properties of those compositions. Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure. Weight percent, percent by weight, % by weight, wt %, and the like are synonyms that refer to the concentration of a substance as the weight of that substance divided by the weight of the composition and multiplied by 100.

As used in this specification and the appended claims, the singular forms "a," "an," and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of controlling corrosion rate of a crude oil refinery process comprising:
    measuring copper concentration of the crude oil refinery process to establish an initial corrosion rate of the crude oil refinery process;
    measuring pH of the crude oil refinery process;

measuring chloride concentration of the crude oil refinery process;

altering the initial corrosion rate of the crude oil refinery process according to the measured pH and the measured chloride concentration and correcting for dynamic state error, thereby determining an altered corrosion rate;

comparing the altered corrosion rate to a pre-determined range of acceptable values;

if the altered corrosion rate is outside of the pre-determined range of acceptable values, performing a remedial measure to change the altered corrosion rate to a value within the range of acceptable values; and repeating the steps.

2. The method of claim 1, wherein the remedial measure comprises adding to the crude oil refinery process a chemical selected from the group consisting of: a neutralizer, a caustic agent, a filming inhibitor, and combinations thereof.

3. The method of claim 1, wherein the remedial measure comprises adding a neutralizer to the crude oil refinery process.

4. The method of claim 3, wherein the neutralizer is selected from the group consisting of 3-methoxypropylamine, monoethanolamine, N,N-dimethylaminoethanol, methoxyisopropylamine, and combinations thereof.

5. The method of claim 1, wherein the remedial measure comprises adding a caustic agent to the crude oil refinery process.

6. The method of claim 5, wherein the caustic agent is 7.5° to 14° Baume sodium hydroxide solution.

7. The method of claim 1, wherein the remedial measure comprises adding a filming inhibitor to the crude oil refinery process.

8. The method of claim 7, wherein the filming inhibitor is selected from the group consisting of: an oil soluble blend of amides, an oil soluble blend of imidazolines, and an oil soluble blend of amides and imidazolines.

9. The method of claim 1, wherein the altering step comprises performing a regression analysis to determine the altered corrosion rate.

10. A method of controlling corrosion rate of a crude oil refinery process comprising:

measuring copper concentration of the crude oil refinery process to establish an initial corrosion rate of the crude oil refinery process;

measuring pH of the crude oil refinery process;

measuring chloride concentration of the crude oil refinery process;

altering the initial corrosion rate of the crude oil refinery process according to the measured pH and the measured chloride concentration, and correcting for dynamic state error and steady state error, thereby determining an altered corrosion rate;

comparing the altered corrosion rate to a pre-determined range of acceptable values;

if the altered corrosion rate is outside of the pre-determined range of acceptable values, performing a remedial measure to change the altered corrosion rate to a value within the range of acceptable values; and repeating the steps.

11. The method of claim 10, wherein the remedial measure comprises adding to the crude oil refinery process a chemical selected from the group consisting of: a neutralizer, a caustic agent, a filming inhibitor, and combinations thereof.

12. The method of claim 10, wherein the altering step comprises performing a regression analysis to determine the altered corrosion rate.

* * * * *

UNITED STATES PATENT AND TRADEMARK OFFICE
CERTIFICATE OF CORRECTION

PATENT NO.         : 9,834,732 B2
APPLICATION NO.    : 15/284770
DATED              : December 5, 2017
INVENTOR(S)        : Wang et al.

Page 1 of 1

It is certified that error appears in the above-identified patent and that said Letters Patent is hereby corrected as shown below:

On the Title Page

Item (54), please delete "DEVELOPMENT AND IMPLEMENTATION OF ANALYZER BASED CONTROL SYSTEM AND ALGORITHM" and add --DESIGN DEVELOPMENT AND IMPLEMENTATION OF ANALYZER BASED CONTROL SYSTEM AND ALGORITHM--

Signed and Sealed this
Sixth Day of March, 2018

Andrei Iancu
*Director of the United States Patent and Trademark Office*